United States Patent [19]

Andrews et al.

[11] 4,304,894

[45] Dec. 8, 1981

[54] QUATERNARY AMMONIUM TERPOLYMERS

[75] Inventors: John K. Andrews, Harlow; John G. B. Howes, Hertford Heath; Rupert A. Selway, Harlow, all of England

[73] Assignee: Smith & Nephew Pharmaceuticals Ltd., Hertfordshire, England

[21] Appl. No.: 33,541

[22] Filed: Apr. 26, 1979

[30] Foreign Application Priority Data

Apr. 26, 1978 [GB] United Kingdom ............... 16577/78

[51] Int. Cl.³ .................... C08F 14/14; C08F 14/02; C08F 226/04
[52] U.S. Cl. ............................. 526/310; 71/67; 71/85; 422/28; 424/78; 526/248; 526/287; 526/291; 526/293; 526/295; 526/296; 526/317; 526/319
[58] Field of Search .............. 526/310, 295, 291, 248, 526/296, 287, 319, 317, 293

[56] References Cited

U.S. PATENT DOCUMENTS 3,539,684 11/1970 Hoover .................. 424/78

OTHER PUBLICATIONS

Hay—U.S. Pat. No. 3,306,875, cols. 1-2, 35-36.

Primary Examiner—Harold D. Anderson

Attorney, Agent, or Firm—Robert L. Goldberg

[57] ABSTRACT

Watersoluble terpolymers based on three monomer units all of formula:

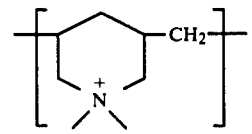

(or possibly the 5-membered ring analogue) wherein the N-substituents are respectively (A) low-low e.g. dimethyl (B) low-medium e.g. methyloctyl and (C) low-higher e.g. methyllauryl or methylcetyl, in molecular size; B:C being usually 5:1 to 0.333:1 (perferably 2:1 to 1:1) in weight ratio, and species less than 10,000 or preferably 20,000 m.w. usually being removed, have surprisingly effective sterilizing activity e.g. against Candida while (a) not accumulating in soft contact lenses, whereby they can be used as an overnight nonirritant aqueous sterilant solution at concentrations below 0.1 weight percent e.g. 0.05 or less and (b) not penetrating skin or like membrane whereby aqueous formulations can be used as topical disinfectants without systemic side-effects.

14 Claims, 7 Drawing Figures

QUATERNARY AMMONIUM TERPOLYMERS

This invention relates to a novel class of watersoluble polymeric materials exhibiting quaternary ammonium groups, and to the use of the bactericidal properties of such materials in the preparation of sterilizing solutions for storage of prostheses such as contact lenses.

Contact lenses have for many years been made of hard polymeric material based predominantly on polymeric methyl methyacrylate. More recently, lenses have alternatively been made of soft material, whether rubbery hydrophobic material such as the silicone-based lenses or hydrophilic material such as the gel-based lenses using e.g. hydroxyethylmethacrylate or like monomers to produce alone or with compatible comonomers a water-swellable polymer.

These lenses are removed each night and placed in a sterilizing solution. For hard lenses, or for hydrophobic soft lenses, the main criterion of such solution is that it shall maintain sterility, at least insofar as that term is understood ophthalmically. For hydrophilic soft lenses, however, additional criteria apply; thus the solution shall not be such as to affect the water content of the lens (and thus its dimensions) or, more importantly, shall not contain any dissolved material which can be absorbed by the lens and lead to irritation or damage when the lens is subsequently worn.

Unfortunately, common bactericidal materials such as chlorhexidine or benzalkonium chloride do exhibit a tendency to accumulate in a soft contact lens with consequent irritation to the wearer. Because of this, the upper practical concentration which can be used without unacceptable irritation is one at which their biocidal activities are considerably diminished, as explained below.

U.S. Pat. No. 3,539,684 describes water-soluble polymeric quaternary ammonium compounds, active against *Aerobacter aerogenes* and useful to sterilize cooling water towers, ponds, reservoirs or swimming pools to inhibit algal or bacterial growth. These compounds are said to be based upon monomer units of formula

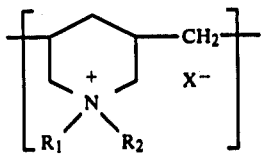

although the analogous 5 membered ring structure

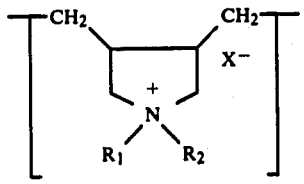

has been proposed. Nonetheless, for convenience herein the above 6 membered ring structure will also be used to define the novel products of the present invention.

In the formula, X is any convenient anion and basically $R_1$ is a small alkyl group (e.g. $CH_3$) and $R_2$ a large (e.g. $C_8$). The inventors also envisage copolymers of two such monomers, one where $R_1$ and $R_2$ are both small alkyl groups and the other where one such group is small and one large.

In one aspect of the invention we have now discovered that by modifying such a polymer structure still further so as to provide a terpolymer (or higher order polymer) with three distinct pairs of substituted on the nitrogen atom a novel water-soluble polymer can be made which is useful for example in a sterilizing solution for contact lenses, especially soft hydrophilic contact lenses, but which also provides the other uses outlined in this specification.

In one aspect the present invention provides a water-soluble polymeric material wherein a major amount, and preferably at least 90% by weight of the monomer units consist of (A) (B) and (C) units, as defined below, the 0–10% remainder by weight being units of one or more compatible monomers capable of copolymerisation, and no component (A) (B) or (C) being present in an amount less than 2% by weight.

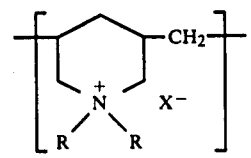

A:

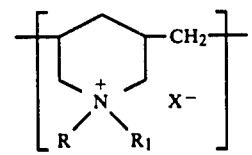

B:

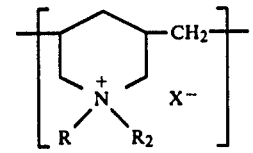

C:

wherein

X is any compatible anion allowing water-solubility,

R is unsubstituted alkyl, or monohydroxyalkyl, the alkyl group in each case containing from one to four carbon atoms, $R_1$ is either (a) unsubstituted alkyl or monohydroxyalkyl the alkyl group in each case containing at least six carbon atoms or (b) a carbocyclic or heterocyclic mononuclear unsubstituted aryl group separated from the nitrogen atom by an unsubstituted or alkyl substituted alkylene group, containing in total up to six carbon atoms, $R_2$ is different from $R_1$, and (i) where $R_1$ is as defined at (a) is either as defined at (b) or is unsubstituted alkyl, or monohydroxyalkyl the alkyl group in this case containing at least eight carbon atoms, and always at least one more carbon atom than $R_1$ as defined at (a) or, (ii) where R is as defined at (b), is as defined at (a).

The R groups may be the same or different. They are usually all the same and all methyl.

The $R_1$ groups are preferably chosen from $C_6$ to $C_{20}$ unsubstituted n-alkyl groups, and more preferably from the $C_6$–$C_{10}$ groups. Specifically, an unsubstituted n-octyl group is preferred for $R_1$.

The $R_2$ groups are preferably chosen from $C_8$ to $C_{20}$ unsubstituted n-alkyl, more preferably from the $C_8$ to $C_{16}$ groups and most specifically are the unsubstituted n-lauryl (C12) or n-cetyl (C16) groups.

$X^-$ may be $F^-$, $Cl^-$, $Br^-$, $I^-$, $CH_3SO_4^-$ or $CH_3COO^-$, but is most preferably $Cl^-$.

Preferably the polymer is a strict terpolymer, i.e. not a higher order copolymer.

The content of units of A can be very low e.g. down to 15% although often it is at least 40%, for example from 50 to 90%, weight percent.

The weight percent ratio between B and C is usually between 5:1 and 1:1, although from 5:1 to 0.333:1 to usable, from 3:1 to 0.5:1 more preferably and from 2:1 to 1:1 optimum.

The content of units B is usually above 3% and can be from 5 to 30% weight percent or more. The contents of units of C is usually above 3% and usually from 3 to 25%; 5% to 20%, weight percent however, is especially useful. However, these are only rough guidelines and viable terpolymers can be produced outside these restricted ranges.

While the novel class of polymer described above is a major aspect of the invention, the use of such polymer in aqueous solution as a sterilizing agent e.g. for contact lenses is another aspect of the invention.

The invention therefore further consists in an aqueous sterilizing solution especially but not exclusively for contact lenses, especially hydrophilic soft contact lenses, which contains one or more of the watersoluble linear polymeric compounds defined above. In commercial practice 0.01% maximum would be especially preferred, but the amount used should exert its effect in a reasonable overnight sterilizing time, e.g. 4 hours maximum. Thus, 0.02% or even 0.05% solutions are still valuable, especially since we have found the active biocidal agent of this solution to have a lower tendency to migrate into and bind to the lens material which we believe is due to its large molecular size compared to that of chlorhexidine or benzalkonium chlorides. Also, because it can be used at higher concentrations without irritation it exhibits useful antifungal effects as well, without the use of an antifungal microbial agent e.g. an organic mercurial.

The novel terpolymers of the invention are of course claimed per se. In use, for the purposes outlined herein, we have found that in most cases it is advisable, and in many cases necessary, to avoid low-molecular weight terpolymers, or terpolymers containing a low molecular weight fraction. Thus, a terpolymer as described above free from species of molecular weight less than 10,000, or preferably less than 20,000, is a preferred form of the invention, especially for the medical and disinfectant uses envisaged. Any necessary removal of low molecular weight species can be effected by any conventional method such as dialysis. Freedom from low molecular weight species is believed to confer the desired properties of non-penetration of skin and non-inclusion into gel-type contact lenses.

The preparation and use of polymers according to the invention will be further described with reference to the following examples, the first of which describes a typical preparation and some of the remainder of which compare the properties of the terpolymer as defined above to those of various two-component polymers, or of terpolymers, outside the scope of the present invention.

PREPARATIVE EXAMPLE

PREPARATION OF A TYPICAL POLYQUATERNARY COPOLYMER CONTAINING METHYL AND N-LAURYL GROUPS.

Diallyl methyloctyl ammonium chloride (3.0 g), diallyl methyl lauryl ammonium chloride (1.5 g) and diallyl dimethyl ammonium chloride (5.5 g) were dissolved in distilled water (10 ml) in a 100 ml flask, t-butyl hydroperoxide (0.6 g) was added, and the resultant solution held at 75 degrees under a nitrogen blanket for 45 hrs.

The viscous solution so obtained was poured slowly into acetone (1.2 L) with stirring and the semi-solid precipitate triturated with fresh acetone until fully solidified, filtered and dried at 100 deg centigrade. The resultant solid was redissolved in water (13 ml) and the solution placed in a closed visking tube, and was dialysed against 200 ml of distilled water for 24 hours. This process was repeated using four further 200 ml aliquots, by which time no material could be demonstrated in the dialyzate. The resultant solution was freezed dried to give 6.2 gms of a pale buff solid polymer.

For convenience the polymer is described as "30:1.5 octyl lauryl", to specify the weight percentage of fatty quaternary monomers employed.

EXAMPLES OF PROPERTIES OF MATERIALS.

All the products made were tested by a microbial 'Die Off' Test, in which an aqueous solution of the test polymer was inoculated with a $10^6$ organism/ml challenge of one of four test organisms. At times 2, 4 and 24 hours after inoculation, an aliquot of test solution was removed and subcultured into recovery medium to test for surviving organisms.

EXAMPLE 1

All of the terpolymers of the invention, and the typical comparison terpolymers and bipolymers were bactericidal against a $10^6$ organism/ml challenge of the following bacteria:

| | | |
|---|---|---|
| *Staphylococcus aureus* | NCTC 6571 | (St. a) |
| *Escherichia coli* | NCTC 86 | (E. c) |
| *Pseudomonas aerugin* | NCTC 6750 | (Ps. a) |

Table 1 shows the earliest sample time at which no viable bacteria were removed from test solution of a range of the polymers.

In this and in all subsequent examples of the invention there were used terpolymers the repeating units of which include unsubstituted n-alkyl groups e.g 1=methyl, 8=n-octyl, 12=n-lauryl, 16=-n-cetyl.

TABLE 1

| MONOMER UNITS WEIGHT - PERCENTAGES | | | | | | TIME (Hrs) To reduce a $10^6$/ml challenge to less than 1 organism. | | |
|---|---|---|---|---|---|---|---|---|
| A | (R,R) | B | (R,R1) | C | (R,R2) | St.a. | E.c. | Ps.a. |
| 75 | 1,1 | 25 | 1,12 | 0 | — | <2 | <2 | <2 |
| 50 | 1,1 | 50 | 1,12 | 0 | — | <2 | <2 | <2 |
| 85 | 1,1 | 10 | 1,8 | 5 | 1,12 | <2 | <2 | <2 |
| 70 | 1,1 | 20 | 1,8 | 10 | 1,12 | <2 | <2 | <2 |
| 62.5 | 1,1 | 25 | 1,8 | 12½ | 1,12 | <2 | <2 | <2 |

Thus, all terpolymers and comparison bipolymers in the above Table, tested as 0.01% aqueous solutions show good bactericidal activity. Because all these test materials showed such good bactericidal activity, further examples were compared using the yeast *Candida Albicans* (London School of Hygiene and Tropical Medicine No. 3153) as being a better challenge organism for comparison purposes.

EXAMPLE 2

Various terpolymers according to the invention were tested against a $10^6$/ml challenge of *Candida Albicans* as in Example 1. The results are given in Table 2.

TABLE 2

| Test Solution (W/v) | Monomer Units Weight - Percentages | | | | | | Sample Time (Hrs) After inoculation | | |
|---|---|---|---|---|---|---|---|---|---|
| | A | (R,R) | B | (R,R1) | C | (R,R2) | 2 | 4 | 24 |
| 0.1% | 85 | 1,1 | 5 | 1,8 | 10 | 1,12 | + | + | − |
| 0.05% | | | | | | | + | + | − |
| 0.1% | 85 | 1,1 | 10 | 1,8 | 5 | 1,12 | + | + | − |
| 0.05% | | | | | | | + | + | − |
| 0.1% | 85 | 1,1 | 7.5 | 1,8 | 7.5 | 1,12 | + | + | − |
| 0.05% | | | | | | | + | + | − |
| 0.1% | 85 | 1,1 | 12 | 1,8 | 3 | 1,12 | + | + | − |
| 0.05% | | | | | | | + | + | − |
| *0.1% | 80 | 1,1 | 15 | 1,8 | 5 | 1,12 | + | − | − |
| 0.05% | | | | | | | + | + | − |
| 0.1% | 77.5 | 1,1 | 15 | 1,8 | 7.5 | 1,12 | + | + | − |
| 0.05% | | | | | | | + | + | + |
| *0.1% | 70 | 1,1 | 20 | 1,8 | 10 | 1,12 | + | − | − |
| 0.05% | | | | | | | + | ± | − |
| *0.1% | 65 | 1,1 | 20 | 1,8 | 15 | 1,12 | + | − | − |
| 0.05% | | | | | | | + | + | − |
| *0.1% | 62.5 | 1,1 | 25 | 1,8 | 12.5 | 1,12 | − | − | − |
| 0.05% | | | | | | | + | − | − |
| *0.1% | 55 | 1,1 | 30 | 1,8 | 15 | 1,12 | + | − | − |
| 0.05% | | | | | | | + | ± | − |
| 0.1% | 50 | 1,1 | 25 | 1,8 | 25 | 1,12 | + | + | − |

+ = Viable challenge organisms recovered
± = Some challenge organisms recovered
− = No viable challenge organisms recovered All examples tested showed some antifugal activity, but some were notably more active than others (noted * in Table 2).

EXAMPLE 3

Different terpolymers within the general scope of the invention were tested against a $10^6$/ml challenge of *Candida Albicans*, as in Example 2. Results are given in Table 3.

TABLE 3

| Test Solution | Monomer Units Weight - Percentages | | | | | | Sample Time (Hrs) After inoculation | | |
|---|---|---|---|---|---|---|---|---|---|
| Strength | A | (R,R) | B | (R,R1) | C | (R,R2) | 2 | 4 | 24 |
| 0.1% | 85 | 1,1 | 10 | 1,8 | 5 | 1,16 | + | + | − |
| 0.05% | | | | | | | + | + | − |
| 0.1% | 85 | 1,1 | 7½ | 1,8 | 7½ | 1,16 | + | ± | − |
| 0.1% | 85 | 1,1 | 12 | 1,8 | 3 | 1,16 | + | ± | ± |
| 0.1% | 70 | 1,1 | 20 | 1,8 | 10 | 1,16 | + | + | − |
| 0.05% | | | | | | | + | + | − |
| 0.1% | 62.5 | 1,1 | 25 | 1,8 | 12½ | 1,16 | + | + | − |
| 0.05% | | | | | | | + | + | − |

(Key as for Table 2)

All examples tested showed some Antifugal activity, though not as marked as that of some of the terpolymers in Table 2.

EXAMPLE 4

Further different terpolymers within the general scope of the invention were tested as in Example 3.

TABLE 4

| Test Solution | Monomer Units Weight - Percentages | | | | | | Sample Time | | |
|---|---|---|---|---|---|---|---|---|---|
| Strength | A | (R,R) | B | (R,R1) | C | (R,R2) | 2 | 4 | 24 |
| 0.1% | 70 | 1,1 | 10 | 1,12 | 20 | 1,16 | ± | ± | − |
| 0.05% | | | | | | | + | ± | ± |
| 0.1% | 70 | 1,1 | 20 | 1,12 | 10 | 1,16 | + | + | − |
| 0.05% | | | | | | | + | + | − |
| 0.1% | 55 | 1,1 | 30 | 1,12 | 15 | 1,16 | + | ± | − |
| 0.05% | | | | | | | + | ± | − |
| 0.1% | 55 | 1,1 | 15 | 1,12 | 30 | 1,16 | + | + | − |
| 0.05% | | | | | | | + | + | − |

(Key as for Table 2)

All examples tested showed some antifugal activity.

EXAMPLE 5

Four further terpolymers of the "octyl-lauryl" type described in Example 2 were tested against a $10^6$/ml. *Candida Albicans* challenge, as before. Results were as shown in Table 5.

TABLE 5

| Test Solution Strength % | Monomer Units Weight - Percentages | | | | | | Sample Time (Hours) | | |
|---|---|---|---|---|---|---|---|---|---|
| | A | (R,R) | B | (R,R1) | C | (R,R2) | 2 | 4 | 24 |
| 0.01 | 60 | 1,1 | 20 | 1,8 | 20 | 1,12 | + | − | − |
| 0.02 | | | | | | | − | − | − |
| 0.05 | | | | | | | − | − | − |
| 0.10 | | | | | | | − | − | − |
| 0.01 | 47.5 | 1,1 | 7.5 | 1,8 | 35 | 1,12 | + | − | − |
| 0.02 | | | | | | | + | − | − |
| 0.05 | | | | | | | + | − | − |
| 0.10 | | | | | | | − | − | − |
| 0.01 | 50 | 1,1 | 37.5 | 1,8 | 12.5 | 1,12 | + | + | − |
| 0.02 | | | | | | | + | + | − |
| 0.05 | | | | | | | + | − | − |
| 0.10 | | | | | | | − | − | − |
| 0.01 | 62.5 | 1,1 | 25 | 1,8 | 12.5 | 1,12 | + | . | − |
| 0.02 | | | | | | | + | − | − |
| 0.05 | | | | | | | . | − | − |
| 0.10 | | | | | | | + | − | − |
| 0.01 | 17.5 | 1,1 | 55 | 1,8 | 27.5 | 1,12 | − | − | − |
| 0.02 | | | | | | | + | − | − |
| 0.05 | | | | | | | − | − | − |
| 0.10 | | | | | | | − | − | − |

Key as before. A dot entry signifies no information available or deducible.

EXAMPLE 6 (COMPARATIVE)

Certain terpolymers outside the scope of the invention were tested as before against *Candida Albicans*.

In this example "HE" means that 2-hydroxy-ethyl radical is used in place of radical $R_2$. Thus the terpolymer in question is deficient by not possing a true $R_2$ radical.

Also "PEG"-means a polythylene glycol radical $(CH_2 CH_2O)$ n where n is about 4.72 on average. This also does not fit the definition of $R_2$, $R_1$, or R.

TABLE 6

| Monomer Units Weight Percentage | | | | | | Sample Time (Hrs) | | |
|---|---|---|---|---|---|---|---|---|
| A | (R,R) | B | (R,R1) | C | (R,R2) | 2 | 4 | 24 |
| 85 | 1,1 | 10 | 1,8 | 5 | 1,HE | + | + | ± |
| 85 | 1,1 | 10 | 1,8 | 5 | 1,HE | + | + | − |
| 85 | 1,1 | 10 | 1,8 | 5 | 1,HE | + | + | − |

TABLE 6-continued

| Monomer Units Weight Percentage | | | | | | Sample Time (Hrs) | | |
|---|---|---|---|---|---|---|---|---|
| A | (R,R) | B | (R,R1) | C | (R,R2) | 2 | 4 | 24 |
| 80 | 1,1 | 10 | 1,16 | 5 | 1,PEG | + | + | − |

All examples were tested as 0.1% solutions. Only slight antifungal activity was demonstrated.

EXAMPLE 7 (COMPARATIVE)

Other bipolymers containing n-octyl groups were tested against a $10^6$/ml challenge of *Candida Albicans*. Results are given in Table 7

TABLE 7

| MONOMER UNITS WEIGHT PERCENTAGES | | | | | | SAMPLE TIME (Hrs) | | |
|---|---|---|---|---|---|---|---|---|
| A | (R,R) | B | (R,R1) | C | (R,R2) | 2 | 4 | 24 |
| 90 | 1,1 | 10 | 1,8 | 0 | — | + | + | − |
| 85 | 1,1 | 15 | 1,8 | 0 | — | + | + | − |
| 80 | 1,1 | 20 | 1,8 | 0 | — | + | + | − |
| 75 | 1,1 | 25 | 1,8 | 0 | — | + | + | − |
| 50 | 1,1 | 50 | 1,8 | 0 | — | + | + | − |

All examples tested as 0.1% aqueous solutions. Some antifungal activity was demonstrated. No viable organisms were recovered after 24 hours exposure to the test bipolymer.

EXAMPLE 8 (COMPARATIVE)

Other bipolymers were chosen to reproduce as exactly as possible the polymer types of Example 5, i.e. with the same weight of protruding chains by omission of one or other substituted unit and its weight replacement by the remaining unit. The polymer compositions, and results against a $10^6$ *Candida Albicans* challenge are shown in Table 8 it being understood that lines 1 and 2 of this Table describe two bipolymers structurally equivalent to each other and to that described in line 1 of Table 5: lines 3 and 4 to line 2 thereof; lines 5 and 6 to line 3; and lines 7 and 8 to line 4 of Table 5.

TABLE 8

| Test Solution Strength % | Monomer Units Weight - Percentages | | | | | | Sample Time (Hours) | | |
|---|---|---|---|---|---|---|---|---|---|
| | A | (R, R) | B | (R, R1) | C | (R, R2) | 2 | 4 | 24 |
| 0.01 | 55.32 | 1,1 | 44.68 | 1,8 | 0 | 1,12 | + | + | − |
| 0.02 | | | | | | | + | + | − |
| 0.10 | | | | | | | + | + | − |
| 0.01 | 62.79 | 1,1 | 0 | 1,8 | 36.21 | 1,12 | + | + | − |
| 0.02 | | | | | | | − | − | − |
| 0.10 | | | | | | | − | − | − |
| 0.01 | 39.33 | 1,1 | 60.67 | 1,8 | 0 | 1,12 | + | + | − |
| 0.02 | | | | | | | + | + | − |
| 0.10 | | | | | | | + | + | − |
| 0.01 | 50.83 | 1,1 | 0 | 1,8 | 49.17 | 1,12 | + | + | − |
| 0.02 | | | | | | | + | − | − |
| 0.10 | | | | | | | . | . | − |
| 0.01 | 44.06 | 1,1 | 55.94 | 1,8 | 0 | 1,12 | + | + | − |
| 0.02 | | | | | | | + | + | = |
| 0.05 | | | | | | | + | + | − |
| 0.10 | | | | | | | + | + | − |
| 0.01 | 57.09 | 1,1 | 0 | 1,8 | 42.91 | 1,12 | . | . | − |
| 0.02 | | | | | | | − | − | − |
| 0.05 | | | | | | | − | − | − |
| 0.10 | | | | | | | − | − | − |
| 0.01 | 59.56 | 1,1 | 40.44 | 1,8 | 0 | 1,12 | + | + | − |
| 0.02 | | | | | | | + | + | − |
| 0.10 | | | | | | | + | + | − |
| 0.01 | 67.22 | 1,1 | 0 | 1,8 | 32,78 | 1,12 | + | + | − |
| 0.02 | | | | | | | + | + | − |

TABLE 8-continued

| Test Solution Strength % | Monomer Units Weight - Percentages | | | | | | Sample Time (Hours) | | |
|---|---|---|---|---|---|---|---|---|---|
| | A | (R, R) | B | (R, R1) | C | (R, R2) | 2 | 4 | 24 |
| 0.10 | | | | | | | . | . | − |

From a comparison of Tables 8 and 5 it can be deduced that the "octyl-lauryl" terpolymer is always more active than the "octyl" bipolymer and usually more active than the corresponding "lauryl" bipolymer, except for the 3:1 terpolymer and other less preferred ranges.

The invention described above, and in particular the numerical limitations and their relationship to the results obtained on testing, will be more fully described with reference to the accompanying drawings in which.

Figure 1:
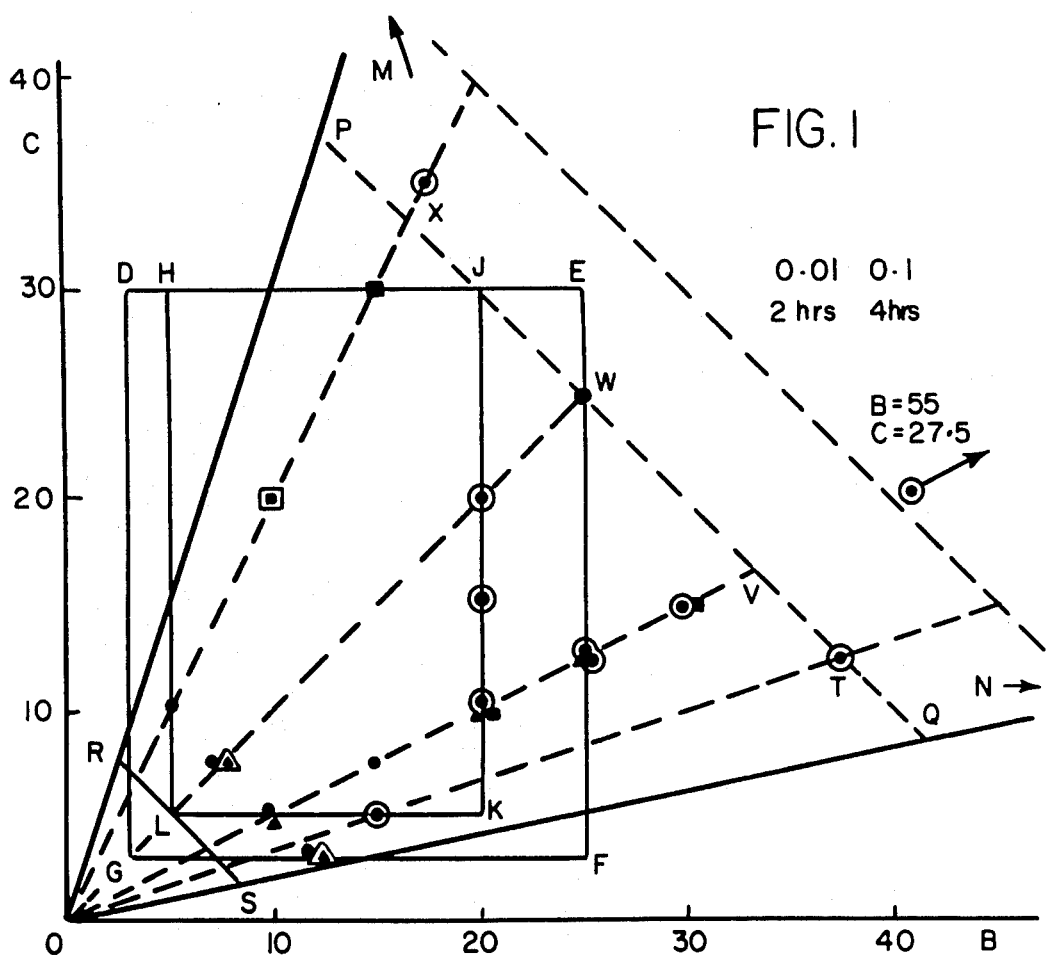
FIG. 1 is a graph of weight percentage of R,R1 monomer units against that of R,R2 monomer units.
Figure 2:
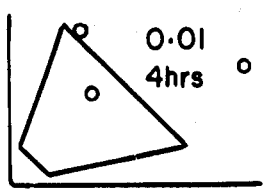
FIGS. 2-7 are diagrammatic graphs indicating how results change if the terpolymers defined by the points on FIG. 1 are used at different strengths and for different times.
Figure 3:
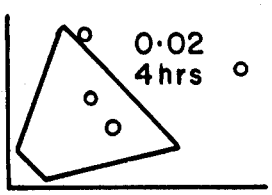

In FIG. 1, each terpolymer is marked with a solid circle, triangle or square, it being understood that if two or more polymers of the same weight ratios are shown they are slightly displaced equally around their true position. Circles denote "octyl-lauryl" terpolymers; triangles "octyl-cetyl" and squares "lauryl-cetyl".

From the tables it will be seen that all or substantially all the terpolymers are active enough to kill all the challenge organisms after 24 hours; this accordingly does not figure on the graph. From the tables moreover, it can be seen that the strongest conditions otherwise measured are for terpolymer at 0.10% concentration for four hours. In instances where this leads to a complete or substantially complete kill of the Candida organism, the point position is shown surrounded by an enclosure of the same shape. Thus, it is quite clear by inspection that the "octyl-lauryl" terpolymer (circles) is the most effective, especially at higher "octyl" and "lauryl" contents; some "octyl-cetyl" (triangles) or "lauryl-cetyl" (squares) terpolymers are active, but usually at low contents of these constituents.

Figure 4:
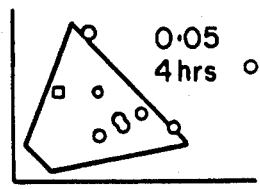
Figure 5:
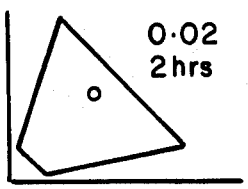
Figure 6:
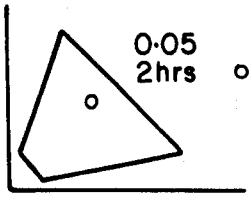
Figure 7:
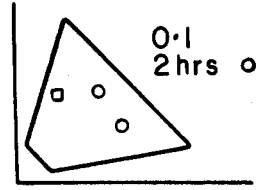

FIGS. 2 to 7 show on a reduced scale only those examples which are active at a variety of other conditions. At 0.01% for four hours three examples are active (FIG. 2), at 0.02% for four hours, four (FIG. 3); and at 0.05% for four hours, nine (FIG. 4). Similarly at 0.02% for two hours only two are active (FIG. 5); two are active at 0.05% (FIG. 6); and by 0.01% at two hours, four are active (FIG. 7). Tentatively therefore from these graphs we can surmise that time of contact is more controlling than concentration: or in other words that with attractively weak solutions a four hour time scale (easily available with overnight lens sterilization) is ample.

For completeness, it is noted that at 0.10% and four hours, 13 compounds are active, while at 0.01% and two hours, only one is namely the 55:27.5 "octyl-lauryl" terpolymer.

The compounds shown, and their activities are not randomly distributed and appear to take up some population or clusters. These can be delimited either by reference to the absolute composition of the polymer, or preferably to the relative proportions of its components.

As to the first, the content of B has already been stated to be usually above 3%, preferably 5–30%, and that of C usually above 3%, preferably 3–25%, most preferably 5–20%. Thus from a consideration of FIG. 1 it can be seen that the rectangle DEFG defines a customary range of compositions and that the rectangle HJKL defines a preferred range. However, there are useful and active compounds outside these ranges.

The content of A is usually but not always at least 40%, preferably 50 to 90%. These limits are shown, in the form of diagram given, as diagonal lines MN, PQ, RS respectively.

As to the second, relative contents of B to C are shown as lines sloping upward from the origin. OQ is 5:1, OT 3:1, OV 2:1, OW 1:1, OX 0:5:1 and OP 0.333:1. Initially this invention was considered to be usually confined between a 5:1 and 1:1 ratio, but we now believe that from 5:1 to 0.333:1 is also a useful definition and indeed FIGS. 2 to 7 show the trapezium PRSQ defined by 5:1 to 0.333:1 as B:C, and 50–90% A as a useful overall preferred area. Again this is not exclusive of other active compounds.

Within the ranges given, those from 3:1 to 0.5:1 are preferred, especially those from 2:1 to 1:1, which contain most of the valuable compositions.

The terpolymers defined above and exemplified, which are themselves novel compounds, generally possess the following advantages: (a) they do not accumulate in a soft contact lense to an undesired extent to lead to irritation even at concentrations of 0.10%, possibly because of the molecular size and shape; moreover, many examples are effective in four hours at 0.05% or less, considerably weaker solutions than those used for chlorhexidine or benzalkonium salts. (b) they are not generally absorbed through the skin and other biological membranes again possibly due to molecular size and shape; thus the chance of systemic toxicity is greatly reduced.

These properties suggest that the compounds of the present invention can also be used for topical application for humans, for example skin sterilizing agents, or for the treatment of microbial infections of skin or of mucous membranes. They could be formulated with pharmacologically acceptable carrier, e.g. liquids, ointments, or lotions. Such new medical uses constitute a further aspect of the invention.

We claim:

1. A watersoluble polymeric material wherein at least 90% by weight of the recurring monomer units consist of (A) (B) and (C) recurring units, as defined below, the 0–10% remainder by weight being units of one or more compatible monomers capable of copolymerisation, and no component (A) (B) or (C) being present in an amount less than 2% by weight:

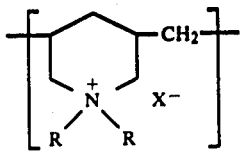
A:

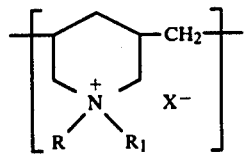
B:

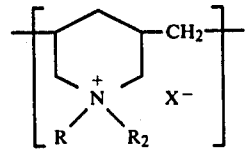
C:

Wherein
X is any compatible anion allowing water-solubility,
R is unsubstituted alkyl, or monohydroxyalkyl, the alkyl group in each case containing from one to four carbon atoms,
$R_1$ is either (a) unsubstituted alkyl or monohydroxyalkyl the alkyl group in each case containing at least six carbon atoms or (b) a carbocyclic or heterocyclic mononuclear unsubstituted aryl group separated from the nitrogen atom of the piperidine ring by an unsubstituted alkylene group, containing in total up to six carbon atoms,
$R_2$ is different from $R_1$, and (i) where $R_1$ is as defined at (a) is either as defined at (b) or is unsubstituted alkyl, or monohydroxyalkyl the alkyl group in this case containing at least eight carbon atoms, and always at least one more carbon atom than $R_1$ as defined at (a) or, (ii) where R is as defined at (b), is as defined at (a).

2. A watersoluble polymer as claimed in claim 1 wherein substantially all of the recurring monomer units consist of (A) (B) and (C) recurring units as defined therein.

3. A watersoluble polymer as claimed in claim 2 wherein the R groups are all methyl.

4. A watersoluble polymer as claimed in claim 3 wherein the $R_1$ group is chosen from $C_6$ to $C_{20}$ unsubstituted n-alkyl groups.

5. A watersoluble polymer as claimed in claim 3 wherein $R_1$ is n-octyl.

6. A watersoluble polymer as claimed in claim 3 wherein $R_2$ is chosen from $C_8$ to $C_{20}$ unsubstituted n-alkyl groups.

7. A watersoluble polymer as claimed in claim 6 wherein $R_2$ is n-lauryl or n-cetyl.

8. A watersoluble polymer as claimed in claim 3 wherein $X^-$ is $Cl^-$.

9. A watersoluble polymer as claimed in claim 3 wherein the weight ratio between R, $R_1$-substituted monomer units and R, $R_2$-substituted units is from 5:1 to 0.333:1.

10. A watersoluble polymer as claimed in claim 9 in which the said weight ratio is from 3:1 to 0.5:1.

11. A watersoluble polymer as claimed in claim 10 in which the said weight ratio is from 2:1 to 1:1.

12. A watersoluble polymer as claimed in claim 11 in which R is methyl, $R_1$ is octyl and $R_2$ is lauryl.

13. A watersoluble polymer as claimed in claim 12 in which the weight percentage giving the said weight ratio are 55:27.5 or substantially those percentages.

14. A watersoluble polymer as claimed in claim 12 in which the weight percentages giving the said weight ratio are 20:20 or substantially those percentages.

* * * * *